United States Patent
Kundu

(10) Patent No.: US 10,308,257 B2
(45) Date of Patent: Jun. 4, 2019

(54) MONITORING RESPIRATION OF A VEHICLE OPERATOR

(71) Applicant: Hitachi, Ltd., Tokyo (JP)

(72) Inventor: Subrata Kumar Kundu, Farmington Hills, MI (US)

(73) Assignee: Hitachi, Ltd., Tokyo (JP)

( * ) Notice: Subject to any disclaimer, the term of this patent is extended or adjusted under 35 U.S.C. 154(b) by 103 days.

(21) Appl. No.: 15/582,809

(22) Filed: May 1, 2017

(65) Prior Publication Data
US 2018/0312167 A1   Nov. 1, 2018

(51) Int. Cl.
*B60W 40/00*      (2006.01)
*B60W 40/08*      (2012.01)
(Continued)

(52) U.S. Cl.
CPC .......... *B60W 40/08* (2013.01); *A61B 5/0004* (2013.01); *A61B 5/053* (2013.01); *A61B 5/0803* (2013.01); *A61B 5/0809* (2013.01); *A61B 5/0816* (2013.01); *A61B 5/6893* (2013.01); *A61B 5/7278* (2013.01); *A61B 5/7282* (2013.01); *B60W 30/06* (2013.01); *B62D 1/046* (2013.01); *G05D 1/0055* (2013.01);
(Continued)

(58) Field of Classification Search
CPC ...... B60W 40/00; B60W 40/08; B60W 30/00; B60W 30/06; B62D 1/00; B62D 1/046; B62D 1/0055; B62D 1/0088; A61B 5/00; A61B 5/0004; A61B 5/053; A61B 5/0803; A61B 5/0809; A61B 5/0816
See application file for complete search history.

(56) References Cited

U.S. PATENT DOCUMENTS

| | | | |
|---|---|---|---|
| 2014/0276090 A1* | 9/2014 | Breed | A61B 5/18 600/473 |
| 2016/0001781 A1* | 1/2016 | Fung | B60W 40/08 701/36 |

(Continued)

FOREIGN PATENT DOCUMENTS

JP      2013-158593 A      8/2013

OTHER PUBLICATIONS

Subrata Kumar Kundu, et al., "A Wearable Capacitive Sensor for Monitoring Human Respiratory Rate", Japanese Journal of Applied Physics 52, Apr. 22, 2013, p. 1-7. http://dx.doi.org/10.7567/JJAP.52.04CL05.

(Continued)

*Primary Examiner* — Yonel Beaulieu
(74) *Attorney, Agent, or Firm* — Mattingly & Malur, PC

(57) ABSTRACT

In some examples, a system may generate an alternating current signal to one of a first sensor electrode or a second sensor electrode. For instance, the first sensor electrode may be associated with a seatbelt and located adjacent to a torso of a vehicle operator of a vehicle. Further, the second sensor electrode may be positioned to be contacted by or otherwise proximate to another body part of the vehicle operator, such as at least one of an arm, hand, leg, or foot of the vehicle operator. The system may receive from the other one of the first sensor electrode or the second sensor electrode, a signal indicative of a capacitance, and may determine a respiration rate of the vehicle operator based at least partially on the signal indicative of the capacitance.

18 Claims, 10 Drawing Sheets

(51) Int. Cl.
*G01D 1/00* (2006.01)
*B60W 30/00* (2006.01)
*B60W 30/06* (2006.01)
*A61B 5/00* (2006.01)
*B62D 1/00* (2006.01)
*G05D 1/00* (2006.01)
*B62D 1/04* (2006.01)
*A61B 5/053* (2006.01)
*A61B 5/08* (2006.01)

(52) U.S. Cl.
CPC ........ *G05D 1/0088* (2013.01); *A61B 2503/22* (2013.01); *A61B 2562/0214* (2013.01); *B60W 2040/0872* (2013.01); *B60W 2540/26* (2013.01)

(56) References Cited

U.S. PATENT DOCUMENTS

| | | | |
|---|---|---|---|
| 2016/0193918 A1* | 7/2016 | Mochizuki | B60K 28/06 600/300 |
| 2017/0129335 A1* | 5/2017 | Lu | B60K 28/066 |
| 2017/0129397 A1* | 5/2017 | Gee | B60C 5/008 |
| 2017/0296128 A1* | 10/2017 | Aoki | A61B 5/024 |
| 2017/0341658 A1* | 11/2017 | Fung | B60W 40/08 |

OTHER PUBLICATIONS

Bill Howard, "Ford smart car locks your phone when you're stressed or distracted", Jul. 4, 2012. https://www.extremetech.com.

* cited by examiner

MONITORING RESPIRATION OF A VEHICLE OPERATOR

BACKGROUND

Vehicle operators may sometimes experience physical impairment or distress while operating a vehicle, which may endanger other people or the operators themselves. Monitoring the vital signs of vehicle operator may provide useful information for determining the ability of the vehicle operator to continue operating the vehicle. Four primary vital signs reflect essential body functions, namely, respiration rate, pulse rate, blood pressure, and body temperature. Respiration rate may include the number of breaths a person takes per minute. An abnormal respiration rate may indicate a potentially serious clinical event. Continuous monitoring of the respiration of a vehicle operator may help to prevent high-risk situations. However, conventional respiration sensors may be intrusive in nature and/or may be inconvenient for a vehicle operator to use on a regular basis.

SUMMARY

Some implementations include arrangements and techniques for monitoring the respiration of a vehicle operator. In some examples, a system may generate an alternating current signal to one of a first sensor electrode or a second sensor electrode. For instance, the first sensor electrode may be associated with a seatbelt and located adjacent to a torso of a vehicle operator of a vehicle. Further, the second sensor electrode may be positioned to be proximate to another body part of the vehicle operator, such as an arm, hand, leg, or foot of the vehicle operator. The system may receive from the other one of the first sensor electrode or the second sensor electrode, a signal indicative of a capacitance, and may determine a respiration rate of the vehicle operator based at least partially on the signal indicative of the capacitance.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
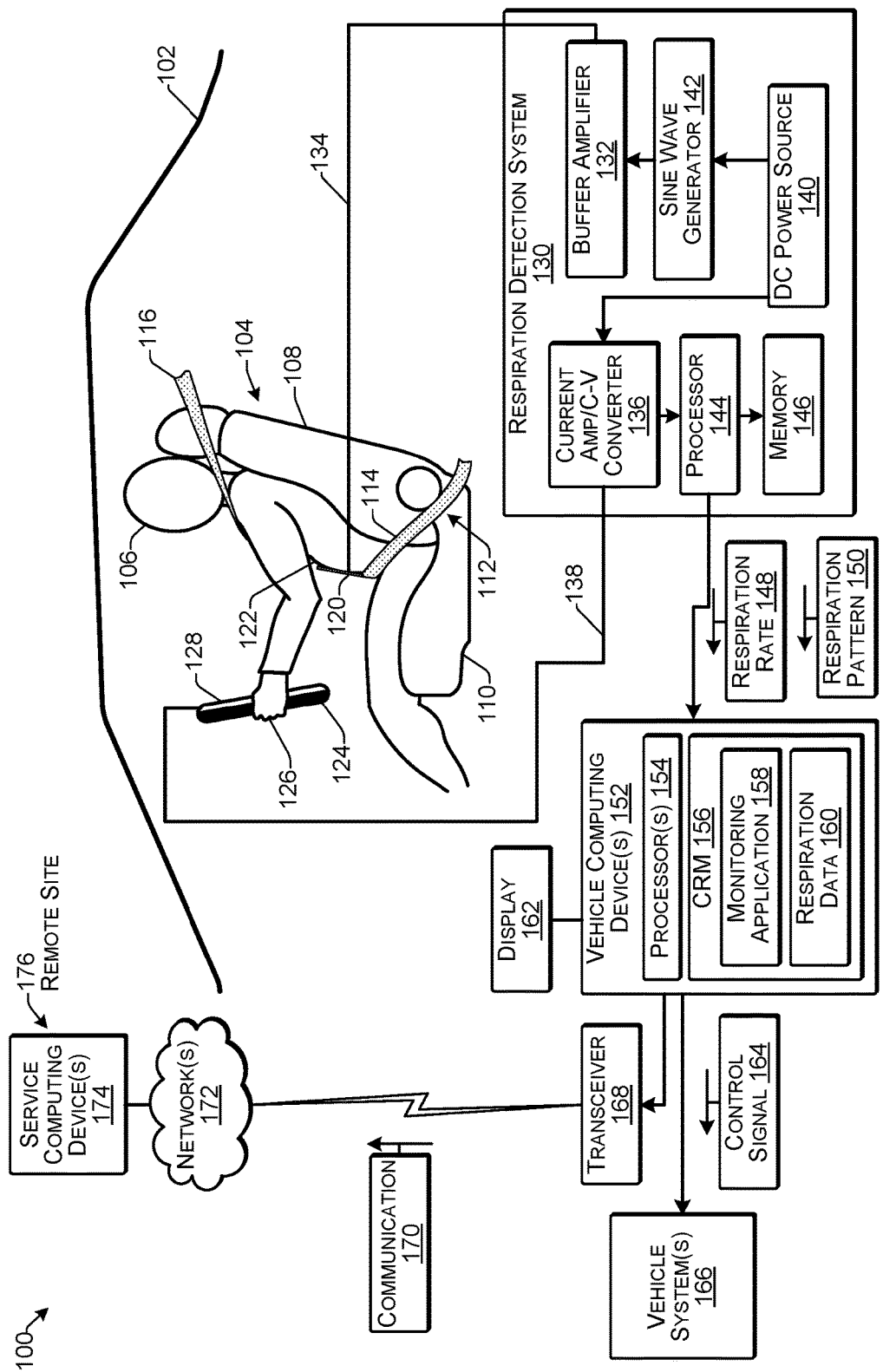
FIG. 1 illustrates an example system for monitoring respiration of a vehicle operator according to some implementations.

The technology herein includes novel arrangements and techniques for monitoring respiration of a vehicle operator. For example, the system herein may be used to determine at least in part whether the vehicle operator is able to continue driving, whether to issue a warning to the vehicle operator, whether to notify a healthcare facility of a condition of the vehicle operator, whether to automatically park the vehicle, whether to take over driving of the vehicle, whether the health of the vehicle operator is deteriorating, or the like. Implementations herein may use a plurality of untethered and convenient sensors incorporated into vehicle components to detect normal and/or abnormal respiration patterns of a vehicle operator. Thus, the system herein does not require the vehicle operator to don intrusive equipment or otherwise inconvenience the vehicle operator.

Some examples provide sensing techniques to measure the respiration rate of a vehicle operator for effectively monitoring the vehicle operator's state. For instance, the respiration sensors herein may be used as one category of sensors for driver state monitoring (DSM). DSM may be included as a subset of Advanced Driver Assistance Systems (ADAS), which are currently being incorporated into vehicles for improving driver safety and comfort. A DSM system may monitor the driver condition/state while operating the vehicle. For example, multiple physiological sensors, including the respiration sensors herein, as well as pulse rate sensors, body temperature sensors, and the like, may be used to monitor the driver's condition, such as for determining the driver's health, fatigue, or stress level. For instance, in the case that an emergency physical condition is detected, the system herein may provide a warning to the driver and/or generate a control signal to control the vehicle. In some cases, information from other physiological sensors, such as sensors for pulse rate, body temperature, or the like, may be used in conjunction with the respiration data when making a determination regarding the physical condition of the vehicle operator.

As mentioned above, the sensors for monitoring vehicle operator respiration herein do not impact driver comfort and do not distract the driver while operating the vehicle. To the contrary, the sensors herein are untethered (i.e., not physically attached to the vehicle operator) and are able to be used for long-term measurement of the respiration of the vehicle operator inside the vehicle. In some examples, the respiration monitoring system herein may include two or more sensor electrodes, such as a first sensor electrode attached to a seatbelt and at least one second sensor electrode located on the steering wheel or at an another position within the vehicle that the driver is likely to contact or otherwise have a body part proximate to. The first sensor electrode located at the seatbelt may generate a first capacitance with the torso of the vehicle operator based on the position of the seatbelt sensor electrode. In addition, the second sensor electrode on the steering wheel may create a second capacitance with a hand of the vehicle operator.

As the vehicle operator operates the vehicle, the second capacitance between the hand and the steering wheel electrode may remain relatively constant, while the first capacitance between the seatbelt electrode and the torso of the operator will change continually due to diaphragm movement and changes in lung volume, which produce expansion and contraction of the operator's torso. This change may be detected through a change of the second capacitance and attributed to the respiration since the second capacitance would otherwise be unchanged due the constant position of the operator's hand relative to the second sensor electrode.

Accordingly, by monitoring the first capacitance and the second capacitance, implementations herein are able to determine a respiration rate and/or respiration pattern of the operator over time. As one example, the respiration monitoring system may include a capacitance-to-voltage converter that may be used to convert the capacitance into a voltage value that can be further processed by a processor, logic circuit, or other voltage measuring circuit for determining a respiration rate based on detected variations in voltage values.

The examples herein may use at least two conductive electrodes to measure the respiration rate by measuring the capacitance from one of the two electrodes. However, the system herein does not rely on the principle of parallel plate capacitance. To the contrary, a first sensor electrode may be placed adjacent to the torso of the vehicle operator and the second sensor electrode may be placed in a location that may contact or otherwise be adjacent to another part of the body of the vehicle operator. In some examples, the second sensor electrode may be placed on the steering wheel of the vehicle, and/or in other locations that the vehicle operator is likely to contact or have a body part proximate to, such as an armrest on the vehicle console, a vehicle gear shifter, a bottom seat cushion, a foot pedal, or the like.

The example sensor locations described herein may be optimized based on user preference and/or sensor effectiveness. Furthermore, the respiration monitoring system herein may not only measure the breathing rate of the operator, but may also be used to determine different breathing patterns based on time scale data analysis, such as by analyzing the respiration rate data collected over a period time, such as several minutes. Additionally, a likely physical condition of the vehicle operator may be determined based on the detected breathing pattern.

If the respiration monitoring system detects abnormal respiration of the vehicle operator, the system may perform one or more actions. For example, the system may warn the driver about a current physical condition indicated by the breathing pattern. Additionally, or alternatively, if the detected respiration data indicates a serious health condition, e.g., extremely high rate of respiration, a control signal may be sent to the vehicle control system as emergency input information such as to cause the vehicle to automatically park itself along the side of the road, or to otherwise take over control of the vehicle from the vehicle operator. In addition, in the case of an emergency situation, the respiration monitoring system may notify a healthcare facility computing device to provide an ambulance or other emergency support for the vehicle operator. In addition, implementations herein may enable the respiration monitoring system to continuously monitor, record, and upload the respiration data over a network to a service computing device that may be associated with a healthcare provider or other service for monitoring the health of the vehicle operator, or the like.

For discussion purposes, some example implementations are described in the environment of monitoring respiration of a vehicle operator. However, implementations herein are not limited to the particular examples provided, and may be extended to other service environments, other vehicle components, other system architectures, other vehicle computing device arrangements, other sensor configurations, and so forth, as will be apparent to those of skill in the art in light of the disclosure herein.

FIG. 1 illustrates an example system 100 for monitoring respiration of a vehicle operator according to some implementations. A vehicle 102 may include a seat 104 in which a vehicle operator 106 may sit while operating the vehicle 102. The seat 104 includes a seatback 108 and a seat bottom 110. A seatbelt 112 may be used to secure the vehicle operator 106 in the seat 104, and may include a lap belt portion 114 and a shoulder belt portion 116. A first sensor electrode 120 may be associated with the seatbelt 112, such as by being secured to at least one of the lap belt portion 114 or the shoulder belt portion 116. Accordingly, when the seatbelt 112 is positioned around the vehicle operator 106, the first sensor electrode 120 is positioned adjacent to the torso 122 (e.g., abdomen and/or chest) of the vehicle operator 106.

In addition, the vehicle 102 includes a steering controller, such as a steering wheel 124, which may be gripped by one or more hands 126 of the vehicle operator 106. At least one second sensor electrode 128 may be included on or otherwise associated with the steering wheel 124 such as for being contacted by, or otherwise being located proximate to, the hand 126 of the vehicle operator 106 when the vehicle operator 106 is holding the steering wheel 124.

Additionally, the vehicle 102 includes a respiration detection system 130 that employs the first sensor electrode 120 and the second sensor electrode 128 for detecting the respiration of the vehicle operator 106. In this example, the respiration detection system 130 includes a buffer amplifier 132 that is connected to the first sensor electrode 120 on the seatbelt 112 by a conductor 134, such as a wire or the like. Further, a current amplifier and capacitance-to-voltage (C-V) converter 136 is connected to the second sensor electrode 128 on the steering wheel by a conductor 138 such as a wire or the like. In other examples, these connections may be reversed, i.e., the buffer amplifier 132 may be connected to the electrode 128 on the steering wheel 124, and the current amplifier/C-V converter 136 may be connected to the sensor electrode 120 on the seatbelt 112.

In addition, the respiration detection system 130 includes a DC (direct-current) power source 140, a sine wave generator 142, a processor 144, and a memory 146. For example, the processor 144 may be a micro control unit (MCU), logic circuit, microprocessor, or the like. In some cases, the current amplifier/C-V converter 136 may include a capacitance-to-voltage converter and the processor 144 may simply be a voltage measurement device able to measure the voltage amplitude as a function of time from the voltage received from the current amplifier/C-V converter 136. In other examples, such as in the case that the processor 144 is an MCU, the processor 144 may determine a variation in capacitance from the current received from the current amplifier 136 without a capacitance-to-voltage converter, and may also perform additional processing functions as discussed additionally below. Numerous other variations will be apparent to those of skill in the art having the benefit of the disclosure herein.

In some cases, the DC power source 140 may be a battery, while in other cases, the DC power source 140 may be a power supply powered by the vehicle power system. In some examples, the DC power source 140 may be a 6 V power source in which the power is converted from the 12 V power of the vehicle power system. The DC power source 140 may supply DC current to the sine wave generator 142, which acts as a signal generator to provide an alternating current to the buffer amplifier 132. The buffer amplifier 132 amplifies the alternating current and provides the amplified alternating current to the sensor electrode 120 at the seatbelt 112.

Breathing is accomplished by inhalation and exhalation through the respiratory system. In inhalation, the diaphragm moves downward, causing the lungs to expand and draw in oxygen-rich air. In exhalation, the diaphragm moves upward, causing the lungs to contract and expel spent air. The changes in lung volume and the corresponding diaphragm movement result in the expansion-contraction of the torso. The entire process from the start of inhalation to the end of exhalation is referred to as a respiration cycle or simply a "breath", and the total number of breaths per minute is referred to as the respiration rate. For healthy adults, the average respiration rate ranges from 12 to 20 breathes per minute. A respiration rate under 12 or over 25 breaths per minute while resting may be considered abnormal.

Since expansion and contraction of the torso occurs during breathing, placement of the first sensor electrode 120 adjacent to the torso 122 of vehicle operator 106 can be used in detecting torso movement during inhalation and exhalation, which is indicative of the respiration rate. Thus, the first sensor electrode 120 associated with the seatbelt 112 positioned close to or otherwise adjacent to torso 122 of the vehicle operator 106 may be used to detect change in capacitance caused by the movement of the torso due to inhalation and exhalation. The second sensor electrode 128 may be placed on the steering wheel 120 or other location that is contacted by or adjacent to a hand or other body part of the vehicle operator 106 that will maintain a constant position for a length of time sufficient to measure the respiration of the vehicle operator. The amount of abdomen/chest expansion-contraction that occurs during inhalation and exhalation varies from human to human. Thus, the optimal location for placement of the first electrode 120 at the seatbelt 112 may vary from vehicle operator to vehicle operator.

The memory 146 may be used to store the output voltage from the current amplifier and/or a measured respiration rate 148 and/or a respiration pattern 150. In addition, the memory 146 may store instructions, such as executable code, a program, an application, firmware, or the like, that may be executed by the processor 144 for determining the respiration rate and/or respiration pattern. For example, the processor 144 may be configured by executable instructions to calculate the respiration rate 148 as a function of time and/or to determine a respiration pattern 150 based on the sensor signal received through the current amplifier/C-V converter 136.

Additionally, the respiration rate 148 and the respiration pattern 150 may be sent to a vehicle computing device 152, such as an electronic control unit (ECU) or other vehicle computing device, processor, or the like. In the illustrated example, the vehicle computing device 152 includes a processor 154 and one or more computer readable media (CRM) 156. The computer readable media 156 includes a monitoring application 158 that is executed by the processor 154 for performing one or more operations based on received respiration data 160, which may include the respiration rate 148 and/or the respiration pattern 150. Furthermore, in some examples, the processor 144 may be the same as the processor 154. For example, the current amplifier/C-V converter 136 may provide the sensed signal from the sensor 128 directly to the processor 154, and the processor 144 may be eliminated.

The vehicle computing device 152 and/or the respiration detection system 130 may be in communication with a display 162 that may be used to display the respiration rate 148 and/or the respiration pattern 150 to the vehicle operator 106. In addition, if an abnormal condition is detected based on the respiration data 160, a message such as a warning, alert, or other communication may be presented on the display 162 and may be viewable by the vehicle operator 106. For instance, the display 162 may be visible to the operator 106 of the vehicle 102, and may display a warning light, a warning message, or other information about the physical condition of the vehicle operator 106 based on the received respiration data 160. In some examples, the display 162 may be integrated into the vehicle 102, such as by being a dashboard display or the like. In other examples, the display 162 may be a separate display associated with the respiration detection system 130. Additionally, or alternatively, the monitoring application 158 may cause one or more speakers (not shown in FIG. 1) to present an audible message to the vehicle operator 106 regarding the sensed condition of the vehicle operator 106.

The monitoring application 158 may determine to perform one or more actions based on the received respiration data 160. For example, if an abnormal respiration pattern is detected, as mentioned above, the monitoring application may present a warning to the vehicle operator 106 on the display 162 and/or may provide an audible alert or the like. Additionally, in the case that the respiration pattern is abnormal to the extent that it may be categorized as a medical emergency, the monitoring application may send a control signal 164 through one or more vehicle systems 166. For example, the one or more vehicle systems 166 may include and ADAS controller that may take over operation of the vehicle from the vehicle operator 106, such as for parking the vehicle 102 as soon as possible, driving the vehicle to an emergency medical facility, or the like.

Alternatively, the vehicle systems 166 may include steering, braking, and throttle systems, and the processor(s) 154 may include the ADAS controller for controlling the vehicle 102. In this configuration, the control signal 164 may include a plurality of control signals for controlling the various systems of the vehicle for parking and/or automatically driving the vehicle.

Additionally, or alternatively, the processor(s) 154 may utilize a transceiver 168 to transmit a communication 170 over one or more networks 172 to one or more service computing devices 174 located at a remote site 176. For example, the service computing devices 174 may be associated with a medical care facility or other service provider who is monitoring the health of the vehicle operator 106. In some examples, the transceiver 168 may be built into the vehicle 102 and may be able to transmit the communication 170 using any suitable wireless transmission techniques such as cellular transmission protocols, Wi-Fi transmission protocols, or any other wireless transmission protocol. In some examples, the service computing device 174 may also include a monitoring program that may notify an emergency medical unit if the vehicle operator 106 is determined to be experiencing a medical emergency, or the like, based on the received communication 170.

In addition, in some examples, the processor(s) 154 may send a communication 170 including the respiration data 160 to the service computing device 174 regardless of whether the respiration pattern is abnormal or not, such as for storage of the respiration data 160 in a medical database, or the like. For instance, the service computing device 174 may be maintained by a medical provider who may monitor the physical health of the vehicle operator 106 based on information received from the sensors included in the vehicle 102. For instance, some examples, the vehicle 102 may include additional sensors such as sensors for measuring body temperature and pulse rate (not shown in FIG. 1) of the vehicle operator 106. Accordingly, sensor information from these additional sensors may be used for correlating the respiration data 160 when determining the physical condition of the vehicle operator 106.

The processor(s) 154 (and in some cases the processor 144) may be implemented as one or more microprocessors, microcomputers, microcontrollers, digital signal processors, central processing units, state machines, logic circuitries, and/or any devices that manipulate signals based on operational instructions. In some cases, the processor(s) 154 may be one or more hardware processors and/or logic circuits of any suitable type specifically programmed or configured to execute the algorithms and processes described herein. The processor(s) 154 may be configured to fetch and execute computer-readable, processor-executable instructions stored in the computer-readable media 156. As one non-limiting example, the processor(s) 154 may include one or more vehicle ECUs or other embedded systems that are connected to the vehicle systems 166, the display 162, the transceiver 168, and/or the respiration detection system 130 via a Controller Area Network (CAN) bus (not shown in FIG. 1).

The one or more computer-readable media 156 (which may include the memory 146 in some examples) may be an example of tangible non-transitory computer storage media and may include volatile and nonvolatile memory and/or removable and non-removable media implemented in any type of technology for storage of information such as computer-readable processor-executable instructions, data structures, program modules, or other data. The computer-readable media 156 may include, but is not limited to, RAM, ROM, EEPROM, flash memory, solid-state storage, magnetic disk storage, optical storage, and/or other computer-readable media technology. Accordingly, the computer-readable media 156 may be computer storage media able to store instructions, modules, or applications that may be executed by the processor(s) 154. Further, when mentioned, non-transitory computer-readable media exclude media such as energy, carrier signals, electromagnetic waves, and signals per se.

As mentioned above, the computer-readable media 156 may be used to store and maintain functional components that are executable by the processor(s) 154. In some implementations, these functional components comprise instructions or programs that are executable by the processor(s) 154 and that, when executed, implement operational logic for performing the actions and services attributed above to the vehicle computing device 104. Functional components of the vehicle computing device 104 stored in the computer-readable media 156 may include the monitoring application 158, which may include a series of instructions and/or executable code for causing the processor(s) 154 to perform the functions described herein. For example, the monitoring application 158 may receive the respiration data 160 from the respiration detection system 130 and may perform one or more actions based on the received respiration data 160.

In addition, the computer-readable media 156 may also store data, data structures, and the like, that are used by the functional component(s). Data stored by the computer readable media 156 may include the respiration data 160, which may be stored temporarily in a buffer prior to being sent to the service computing device 174, or may be stored in a more permanent storage location in the computer readable media 156. As one example, the monitoring application 158 may send the respiration data 160 periodically in batches to the service computing devices 174. Alternatively, the respiration data 160 may be continually streamed to the service computing device(s) 174 if the connectivity of the vehicle computing device 152 to the one or more networks 172 permits such streaming. Further, the vehicle computing device 152 may include other logical, programmatic, and/or physical components, of which those described are merely examples that are related to the discussion herein.

The transceiver 168 is an example of one or more communication interfaces that the vehicle computing device 152 may use for communication with various other devices, such as over the network(s) 172. For example, the transceiver 168 may enable communication through one or more of cellular networks, wireless networks (e.g., Wi-Fi) as well as short-range communications such as BLUETOOTH®, and the like.

The one or more networks 172 may include any network or combination thereof, including a wide area network, such as the Internet; a local area network, such an intranet; a wireless network, such as a cellular network, a local wireless network, such as Wi-Fi and/or short-range wireless communications, such as BLUETOOTH®; a wired network, including fiber optics and Ethernet; or any other such network, or any combination thereof. Accordingly, the one or more networks 172 may include both wired and/or wireless communication technologies. Components used for such communications can depend at least in part upon the type of network, the environment selected, or both. Protocols for communicating over such networks are well known and will not be discussed herein in detail. Accordingly, vehicle computing device 152 and the service computing device(s) 174 are able to communicate over the one or more networks 172 using wired or wireless connections, and combinations thereof.

In some examples, the vehicle computing device 152 may communicate over the network(s) 172 through a cellular communication interface included in the vehicle 102 as the transceiver 168. For instance, many vehicles include a cellular transceiver as standard equipment that may be used to transmit the respiration data 160 from the vehicle computing device 152 to the service computing device(s) 174, such as via one or more cell towers, or the like. Alternatively, the respiration detection system 130 may include a dedicated cellular transceiver (not shown in FIG. 1) for commuting the respiration data 160 directly to the service computing device 174. In some examples, the vehicle computing device 152 may communicate with the service computing device(s) 174 via one or more application programming interfaces (APIs).

Figure 2:
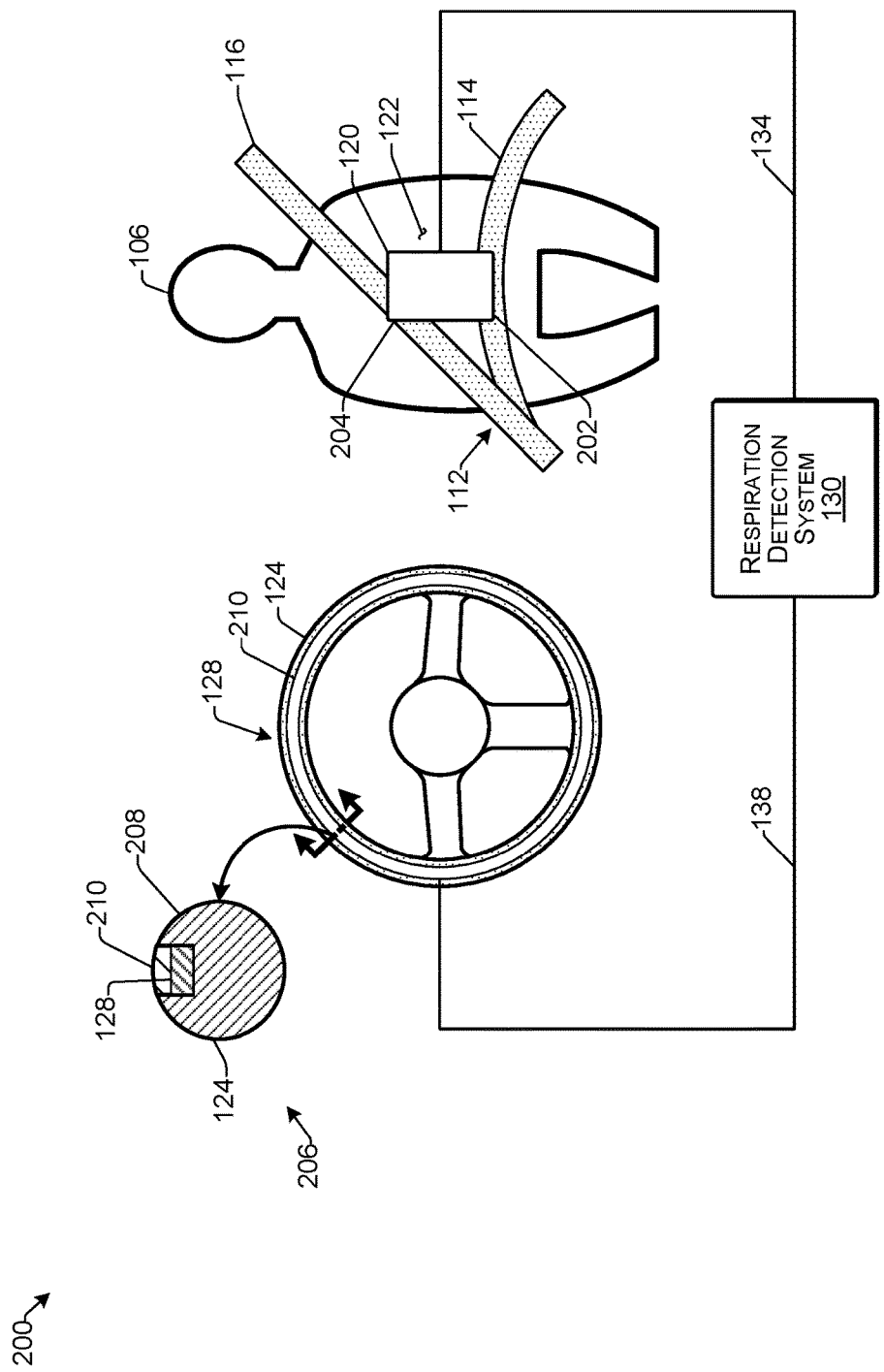
FIG. 2 illustrates example sensors for a system for monitoring respiration of a vehicle operator according to some implementations.

FIG. 2 illustrates an example front view 200 of the sensors of FIG. 1 used electrode for detecting respiration of a vehicle operator according to some implementations. In this example, the first sensor electrode 120 associated with the seatbelt 112 is shown as being rectangular in shape; however any other desired shape such as round, triangular, trapezoidal, rhomboid, diamond-shaped, or so forth, may be used. The first sensor electrode 120 may be connected to the lap belt portion 114 of the seatbelt 112 at 202, and may also be connected to the shoulder belt portion 116 of the seatbelt 112 at 204. In some examples, the first sensor electrode 120 may be connected to the seatbelt portions 114 and/or 116 with one or more loop, or the like, that enable the position of the first sensor electrode 120 to be adjusted relative to the seatbelt portions 114 and 116 to enable the first sensor electrode 120 to be positioned adjacent to the torso 122 of the vehicle operator 106.

The first sensor electrode 120 (and in some examples, the second sensor electrode 128) may be constructed from a conductive material such as copper sheet, aluminum sheet, conductive cloths, or the like. For instance, the first sensor electrode 120 may be generally planar and may be covered with an insulating material, such as a polymer insulator, cello tape, or the like, which may reduce noise and improve safety. The dimensions of the sensor electrodes is a factor that may affect the amplitude of the output voltage from the current amplifier of the respiration measurement system 130. The size and configuration of the first sensor electrode 120 may also be selected based at least in part on the preference of the vehicle operator.

The location for the second sensor electrode 128 may also be determined based at least in part on user preference, as discussed additionally below with respect to FIG. 4. For instance, similar to the first sensor electrode 120, the area of the second sensor electrode 128 may affect the output voltage of the current amplifier and various different shapes might be selected. Other alternative locations for the second sensor electrode 128 are illustrated and discussed below, e.g., with respect to FIG. 4. One difference between the construction/installation of the first sensor electrode 120 and the second sensor electrode 128 is that the second sensor electrode 128 is installed in a manner so that it is not affected by an amount of force applied.

In the example of FIG. 2, the second sensor electrode 128 extends around the circumference of the steering wheel 124. As illustrated by an enlarged cross-sectional cut-away view 206 of FIG. 2, the second sensor electrode 128 may be installed in the steering wheel 124 under the surface the rim 208 of the steering wheel 124, and covered with a thin insulative material 210, such as acrylic or other insulative polymer, or other non-conductive substance, that is not easily deformable by a hand or other human body part. Accordingly, a vehicle operator's finger or thumb may touch only the acrylic plate 210, but not the sensor electrode 128 itself. This construction causes forces due to arm or palm pressure on the acrylic plate to be diminished by the acrylic plate 210 to reduce any movement of the sensor electrode 128 so that the capacitance between the hand and the second sensor electrode 128 will remain substantially constant (discounting the effect of the changes in capacitance between the first sensor electrode and the torso of the vehicle operator).

Figure 3:
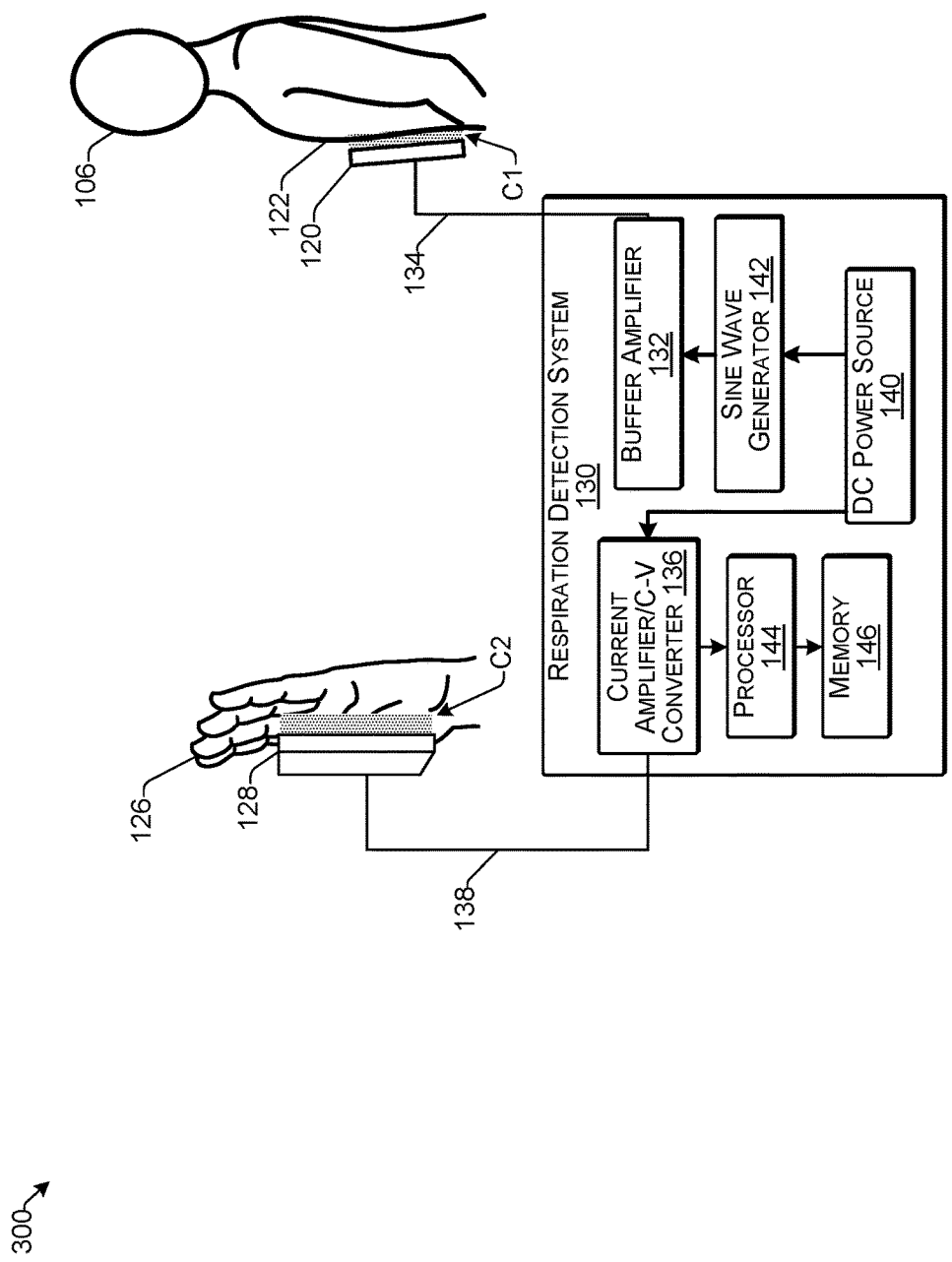
FIG. 3 illustrates an example of capacitive coupling of the sensors according to some implementations.

FIG. 3 illustrates an example 300 of capacitive coupling of the sensor electrodes according to some implementations. In the examples herein, the body of the vehicle operator 106 stores electric charge and may act as a capacitor. Thus, as illustrated in FIG. 3, the first sensor electrode 120 creates a first capacitance C1 with the skin of the vehicle operator's torso 122 (i.e., chest and/or abdomen based on the location of sensor electrode 120 on the seatbelt). Additionally, the second sensor electrode 128 and the skin of the hand 126 of the vehicle operator 106 creates a second capacitance C2. While driving, the second capacitance C2 may remain almost constant when there is no hand movement of the hand 128 in relation to the sensor electrode 128. However, due to the vehicle operator 106 breathing, there will be movement of the torso 122 at the location of the first sensor electrode 120, which changes the first capacitance C1.

While the second capacitance C2 remains almost constant and the first capacitance C1 changes as the torso 122 of the vehicle operator 106 moves during breathing, the respiration rate of the vehicle operator 106 may be detected by monitoring a change in the amplitude of the output voltage from the current amplifier/C-V converter 136 of the respiration detection system 130. The output voltage from the current amplifier/C-V converter 136 may be monitored on a time scale to measure the respiration rate per unit of time and to further determine a respiration pattern based on the respiration rate measured over time.

The function of the sine wave generator 142 is to generate a stable constant sine wave, i.e., an alternating current (AC) signal. The frequency and amplitude of the AC signal may be tuned to optimize the accuracy of detecting the respiration. The buffer amplifier 132 may be a voltage buffer amplifier or a current buffer amplifier that ensures a low output impedance of the excitation sine wave, and may also reduce noise and prevents distortion of the sine wave. Examples of suitable buffer amplifiers include MOSFET type amplifiers and BJT type amplifiers.

The current amplifier/C-V converter 136 may be a current buffer amplifier (MOSFET, BJT, etc.) and may include or be connected to a capacitance-to-voltage converter to convert the small current (which results due to resultant capacitance) into an output voltage. The output voltage from the current amplifier/C-V converter 136 may be monitored by the processor 144, which may include a voltage measurement capability or other voltage measurement circuit, to measure the respiration rate as well as respiration pattern. For instance, the respiration rate may be measured based on the change in the amplitude of the output voltage signal from the current amplifier/C-V converter 136 and the period of the voltage signal.

Figure 4:
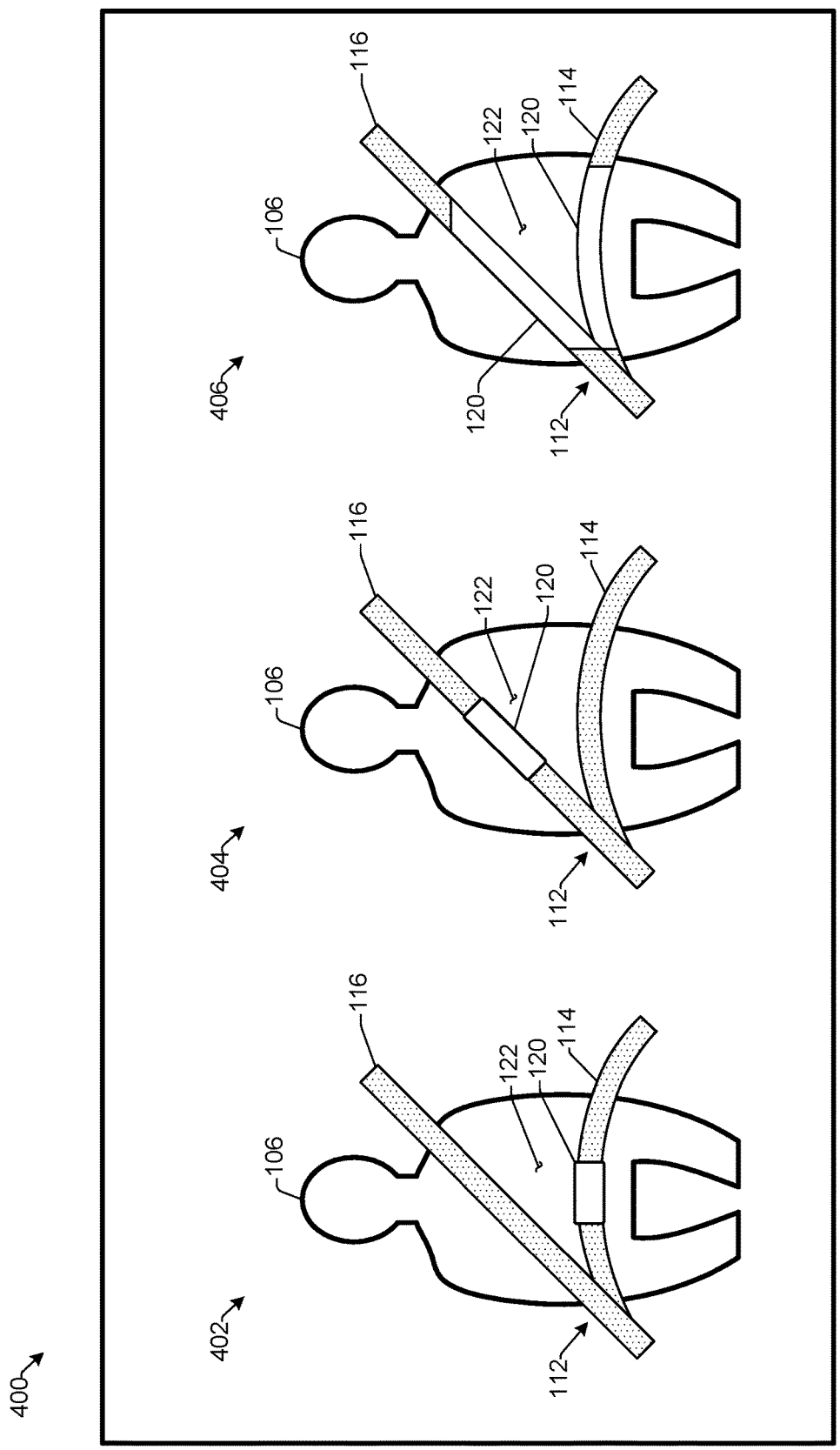
FIG. 4 illustrates examples of sensor configurations for a seatbelt according to some implementations.

FIG. 4 illustrates examples 400 of sensor configurations for seatbelt mounting according to some implementations. The shape and size of the first sensor electrode 120 and the second sensor electrode 128 (not shown in FIG. 4) may be determined based at least partially on the installation location. The overall area of the first sensor electrode 120 and the second sensor electrode 128 may contribute to the accuracy of the respiration measurement. For example, the output voltage of the current amplifier may typically increase with an increase in the area of the sensor electrodes 120, 128. Accordingly, a first sensor electrode 120 having a larger overall area adjacent to the torso 122 of the vehicle operator 106 may result in more accurate respiration measurements than a first sensor electrode 120 having a smaller area, regardless of the shape of the sensor electrode 120.

However, the area of the first sensor electrode 120 may be balanced against other design considerations such as intrusiveness, usability of the seatbelt 112, and so forth. Further, the installation location for the first sensor electrode 120 may be varied based on the preference of the vehicle operator 106, and further based on accuracy resulting from different body shapes. As one constraint, the maximum expansion and contraction area (e.g., on the abdomen or chest of the vehicle operator 106) during breathing may vary from subject to subject. Thus, the first sensor electrode 120 may be placed at different locations based on subject's body function during respiration.

As a first example 402, the first sensor electrode 120 may be incorporated into the lap belt portion 114 of the seatbelt 112. As a second example 404, the first sensor electrode 120 may be incorporated into the shoulder belt portion 116 of the seat belt 112. As still another example, the first sensor electrode 120 may be incorporated into both the lap belt portion 114 and the shoulder belt portion 116 of the seatbelt 112. The first example, 402 may be sufficient for use with many vehicle operators 106, but other vehicle operators 106 may employ other locations of the first sensor electrode 120 for more accurate respiration measurement, such as those illustrated in examples 404, 406, or FIG. 2. The selection of a suitable location of the first sensor electrode 120 may be based at least partially on ensuring that expansion and contraction of the torso 122 results in a force applied to and released from the first sensor electrode 120, respectively, to provide movement thereto. If there is no movement of the first sensor electrode during breathing, then the respiration of the vehicle operator 106 may not be accurately detected.

In some cases, the first sensor electrode 120 may be integrated into the seatbelt 112 by placing the first sensor electrode 120 sandwiched between two layers of the seat belt 112, or by attaching the first sensor electrode 120 to the side of the seatbelt 112 that faces the torso 122. Alternatively, as another example, a portion of the seatbelt may be constructed of a conductive cloth that may serve as the first sensor electrode 120. Numerous other variations will be apparent to those of skill in the art having the benefit of the disclosure herein.

Figure 5:
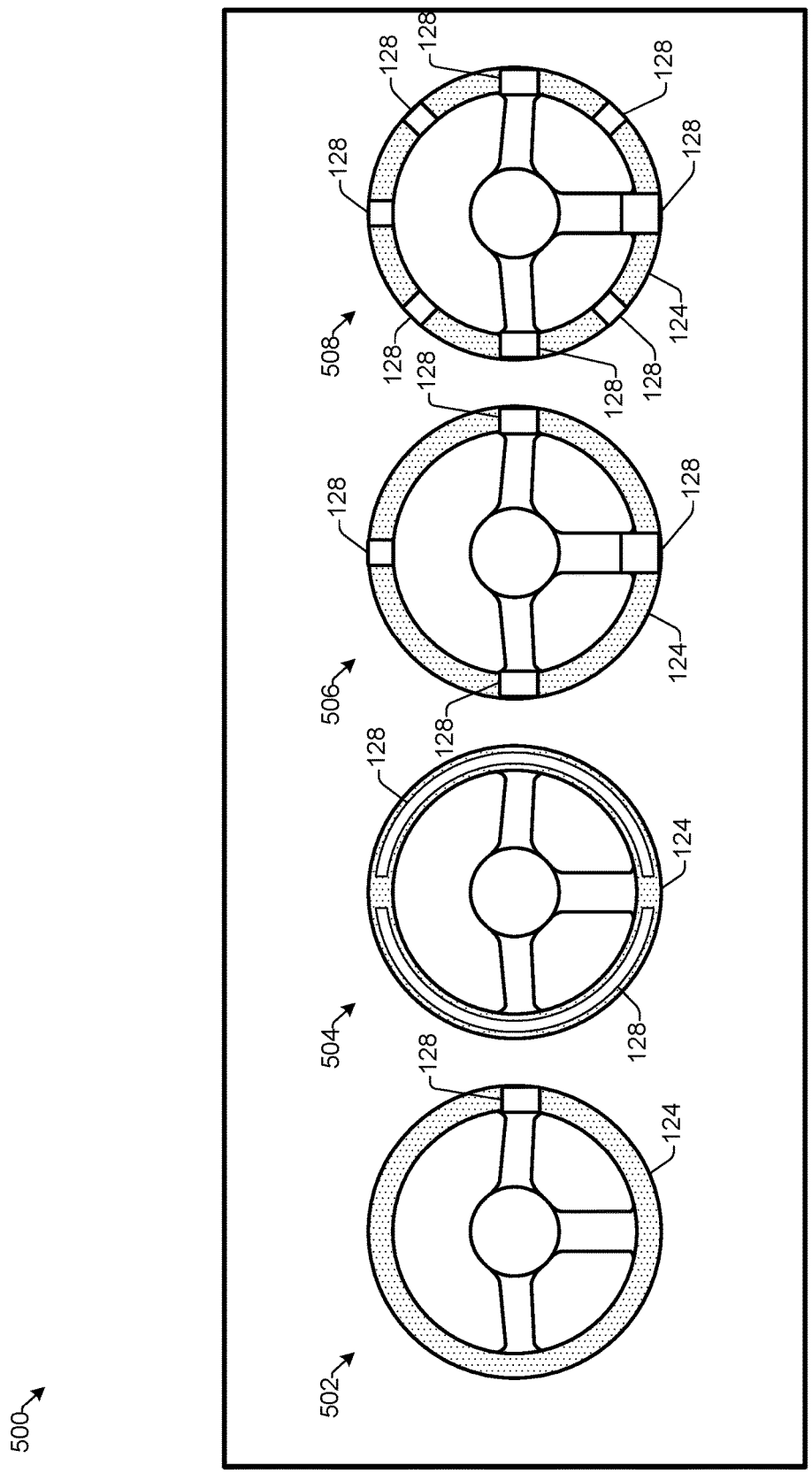
FIG. 5 illustrates examples of sensor configurations for a steering wheel according to some implementations.

FIG. 5 illustrates examples 500 of sensor configurations for a steering wheel according to some implementations. In a first example 502, rather than having the second sensor electrode 128 extend around the entire circumference of the rim of the steering wheel 124, as discussed above with respect to FIG. 2, in this example, the second sensor electrode 128 is embedded in a smaller area on the right side of the steering wheel 124 and covered with an relatively non-deformable insulating material, such as acrylate, or the like, as discussed above. In a second example 504, a pair of semicircular second sensor electrodes 128 extend partially around the circumference of the steering wheel 124, and may also be embedded and covered with an relatively non-deformable insulating material. In a third example 506, a plurality of second sensor electrodes 128 are located radially around the periphery of the steering wheel 124, i.e., at 90 degrees apart from each other, and embedded and covered with an relatively non-deformable insulating material. In a fourth example 508, a larger plurality of second sensor electrodes 128 are located radially around the periphery of the steering wheel 124, i.e., at 45 degrees apart from each other, and embedded and covered with an relatively non-deformable insulating material.

Additionally, while more than one second sensor electrode 128 is shown in the examples 504-508, only one of these second sensor electrodes 128 may typically be used as the second sensor electrode 128 at any particular time. For example, by using resistance or capacitance touch sensing techniques, the processor of the monitoring respiration monitoring system 130 (not shown in FIG. 5) may determine which sensor electrode 128 to use for obtaining the most accurate respiration measurement.

Figure 6:
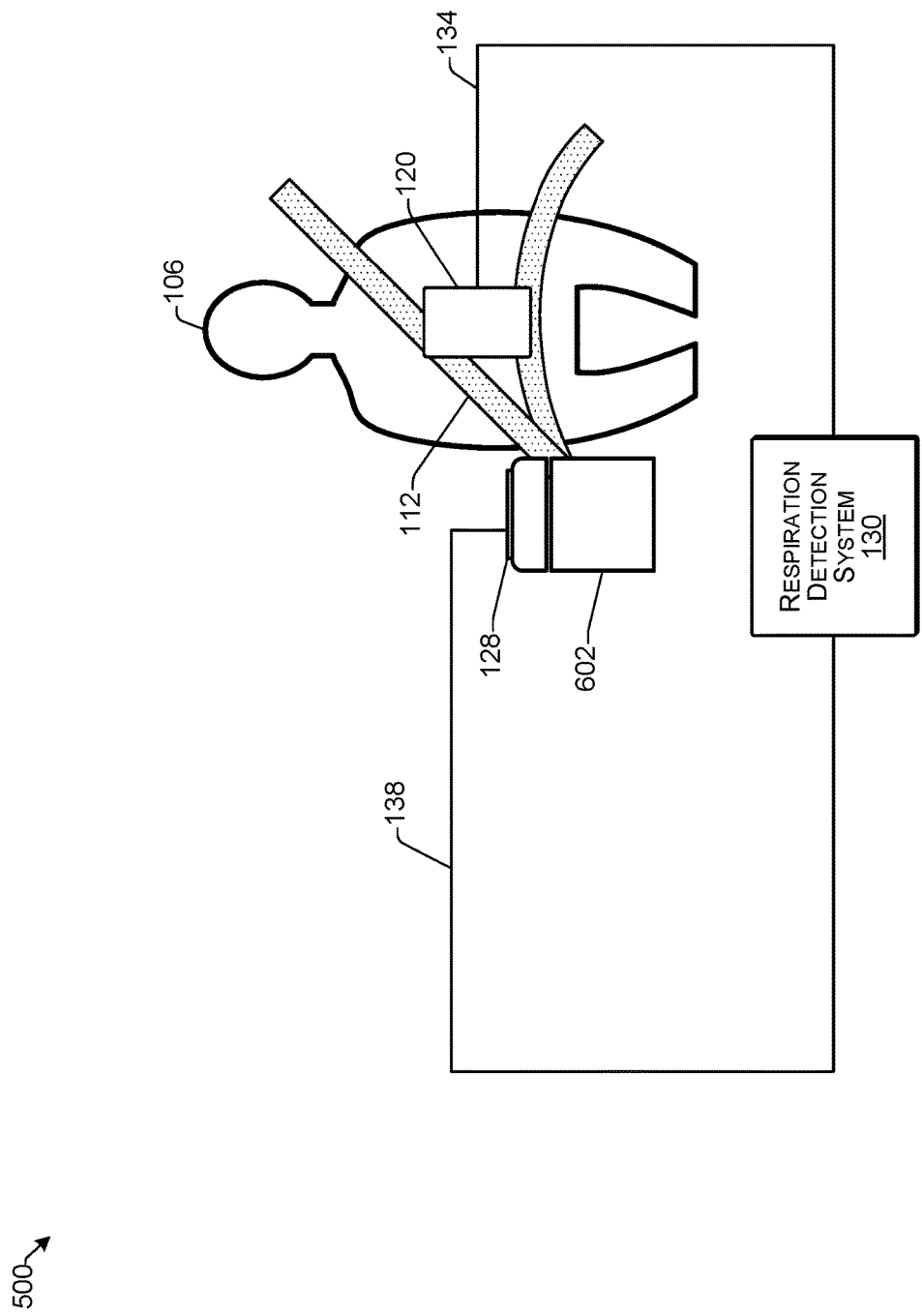
FIG. 6 illustrates an example of a sensor configuration for a vehicle console according to some implementations.

FIG. 6 illustrates an example of a sensor configuration for a vehicle console according to some implementations. For example, rather than, or in addition to, having the second sensor electrode 128 installed on the steering wheel, a second sensor electrode 128 may be installed in a different location within the vehicle, such on the center console armrest 602 of the vehicle. In this case, the second capacitance C2 may be formed between the second sensor electrode 128 and the forearm or elbow of the vehicle operator 106. Furthermore, a force diminishing technique similar to that discussed above may be employed (e.g., an acrylate plate or the like overlying the second sensor electrode 128) to maintain the vehicle operator's forearm consistently immobile with respect to the second sensor electrode 128.

In some examples, to determine the optimal location for the second sensor electrode 128 for any particular user, a constant second capacitance C2 may be initially determined. For instance, a constant second capacitance C2 may be achieved by the vehicle operator 106 placing any finger, palm, etc. on any second sensor electrode 128 electrode, such as on the steering wheel, as discussed above. Additional second sensor electrodes 128 may be placed at different locations for determining the optimal size and location for particular vehicle operators 106. In some cases, the location of the second sensor electrode 128 at which a maximum resultant capacitance is realized may be selected as the optimal location for the second sensor electrode 128. In some examples, the second sensor electrode 120 may be placed on a gear shift lever, a foot pedal, on an upper surface of the bottom seat cushion, and so forth. Furthermore, as mentioned above, when there are multiple second sensor electrodes 128 present in the vehicle, in some examples, the processor of the respiration detection system 130 may determine which of the second sensor electrodes 128 to use at any particular time based on resistance sensing, capacitance sensing, or the like.

Figure 7:
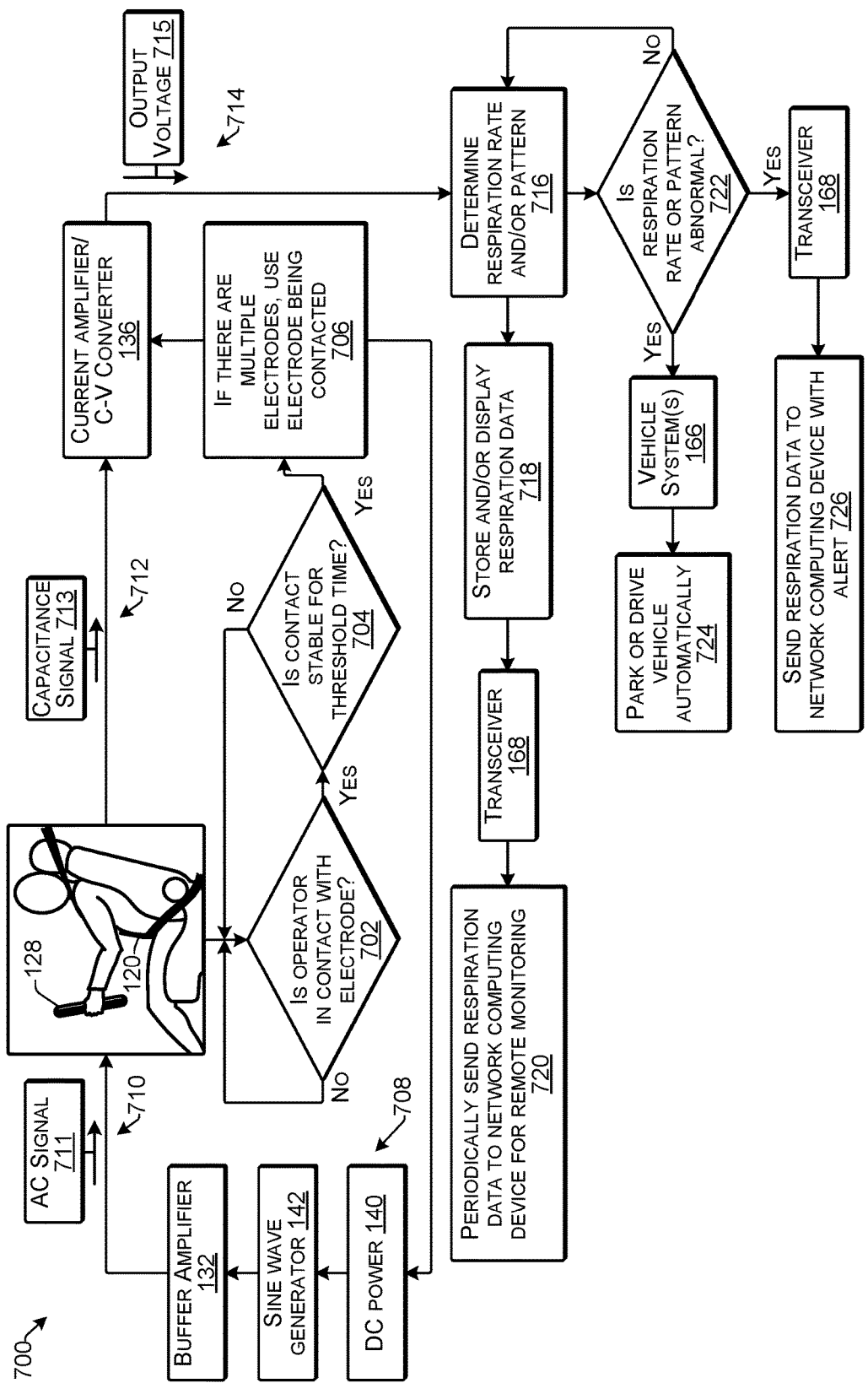
FIG. 7 is a flow diagram illustrating an example process for monitoring respiration according to some implementations.
Figure 9:
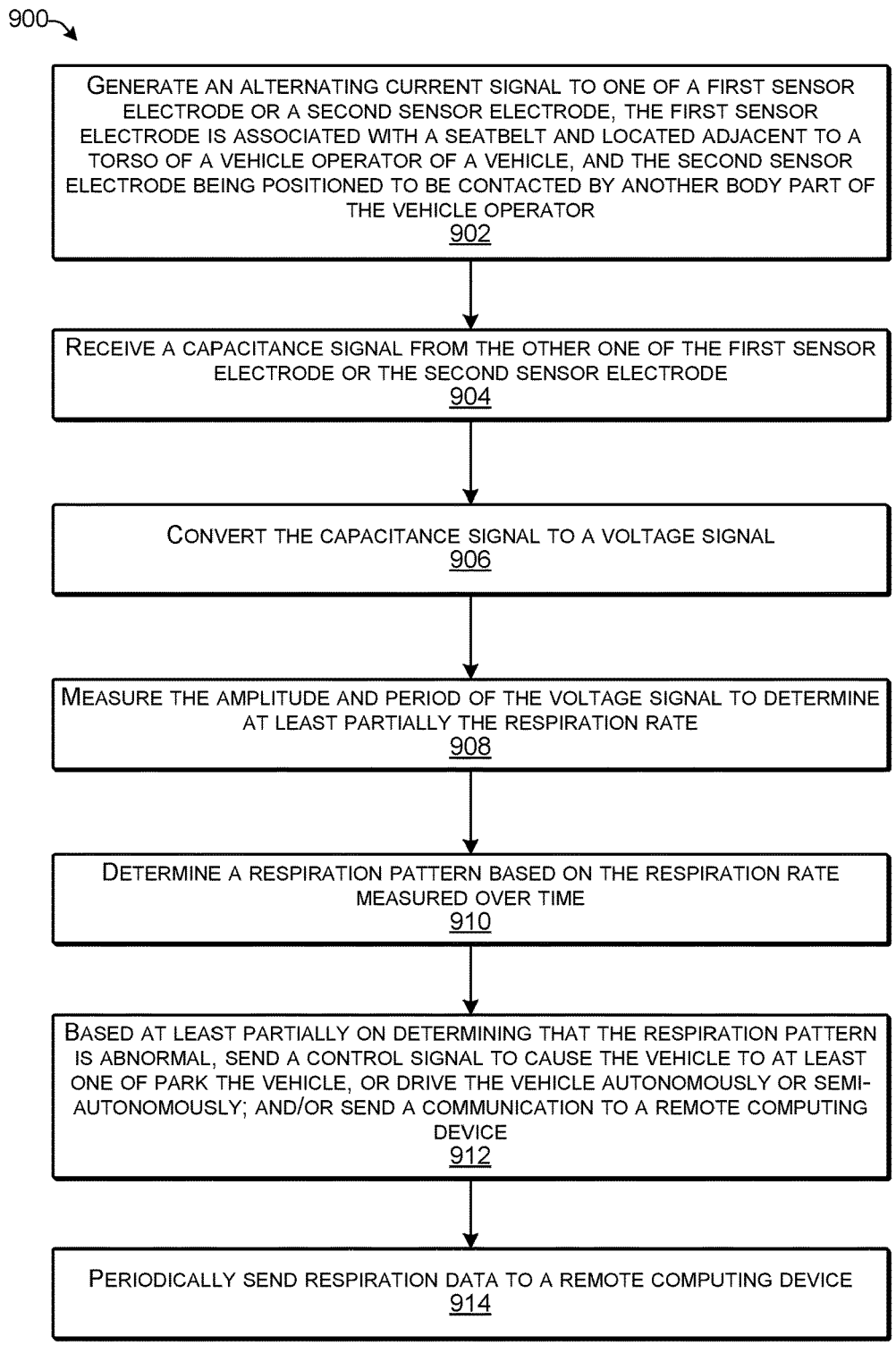
FIG. 9 is a flow diagram illustrating an example process for monitoring respiration according to some implementations.

FIGS. 7 and 9 are flow diagrams illustrating example processes according to some implementations. The processes are illustrated as collections of blocks in logical flow diagrams, which represent a sequence of operations, some or all of which can be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, systems and devices described in the examples herein, although the processes may be implemented in a wide variety of other environments, systems and devices.

FIG. 7 is a flow diagram illustrating an example process 700 for monitoring respiration according to some implementations. For instance, the process may be useful for driver state monitoring system, such as for semi-autonomous vehicles. The process may also be useful for remote monitoring of driver health conditions. The process 700 may be executed, at least in part, by the processor of the respiration monitoring system and/or the processors of the vehicle computing device(s), as discussed above, e.g., with respect to FIG. 1.

At 702, the processor(s) may determine whether the vehicle operator is in contact with a second sensor electrode 128. If so, the process proceeds to 704; if not, the process waits until the vehicle operator is in contact with a second sensor electrode. As mentioned above, contact with a particular second sensor electrode 128 may be detected through a change in capacitance, change in resistance, or the like.

At 704, if the vehicle operator is in contact with the second sensor electrode 128, the processor(s) may determine whether the contact has been stable for a threshold period of time. If so, the process proceeds to 706; in not, the process returns to 702. As a non-limiting example, the threshold period of time may be a number of seconds for determining a breathing rate of the vehicle operator, such as 20 seconds 30 seconds or the like.

At 706, if there are multiple second sensor electrodes, the processor(s) may use the second sensor electrode that is detected as being contacted by the vehicle operator. As mentioned above, the contact may be detected by a change in capacitance, by a change in a resistance measurement, or the like.

At 708, the processor(s) may cause the sine wave generator 142 to receive DC power from the DC power supply 140 and generate a sine wave signal or other alternating current signal to the buffer amplifier 132.

At 710, the buffer amplifier 132 provides an AC signal 711 to one of the sensor electrodes 120 or 128.

At 712, a capacitance signal 713 may be received by the current amplifier/capacitance-to-voltage converter 136 from the other one of the sensor electrodes 120 or 128.

At 714, the current amplifier/C-V converter 136 may convert the capacitance signal 713 into an output voltage 715, and may provide this output voltage to the processor(s).

At 716, the processor(s) may determine a respiration rate and/or a respiration pattern from the output voltage 715.

At 718, the processor(s) may store and/or display respiration data. For example, the respiration data may be stored in a memory on the vehicle. In addition, the respiration data may be presented on a display in the vehicle for viewing by the vehicle operator.

At 720, the processor(s) may use the transceiver 168 to periodically send the respiration data to a network computing device for remote monitoring. For example, the respiration data may be periodically sent to a server or other computing device located over a network. In some examples, the computing device may be a computing device of a healthcare facility, medical provider, or the like, which may monitor the health of the vehicle operator.

At 722, the processor(s) may determine whether the respiration rate and/or respiration pattern is abnormal. Details regarding normal and abnormal respiration patterns are discussed additionally below with respect to FIG. 8.

At 724, if the respiration rate and/or respiration pattern is abnormal, the processor(s) may send a control signal or the like to the vehicle systems 166, such as to an ADAS system or for directly controlling the vehicle systems. The control signal may cause the vehicle to park or drive itself automatically. For example, the vehicle may pull to the side of the road and park the vehicle. Alternatively, the vehicle may drive to the nearest health care facility.

At 726, if the respiration rate and/or respiration pattern is abnormal, the processor(s) may use the transceiver 168 to send respiration data to a network computing device with an alert, which indicates that the vehicle operator is suffering a serious medical condition. In some cases, the alert may include global positioning system (GPS) geolocation information regarding a current location of the vehicle, as determined, e.g., from a GPS receiver present in the vehicle (not shown in FIG. 7). For example, the communication sent to the network computing device may cause the network computing device to dispatch an emergency vehicle to the location of the vehicle operator to provide medical care.

Figure 8:
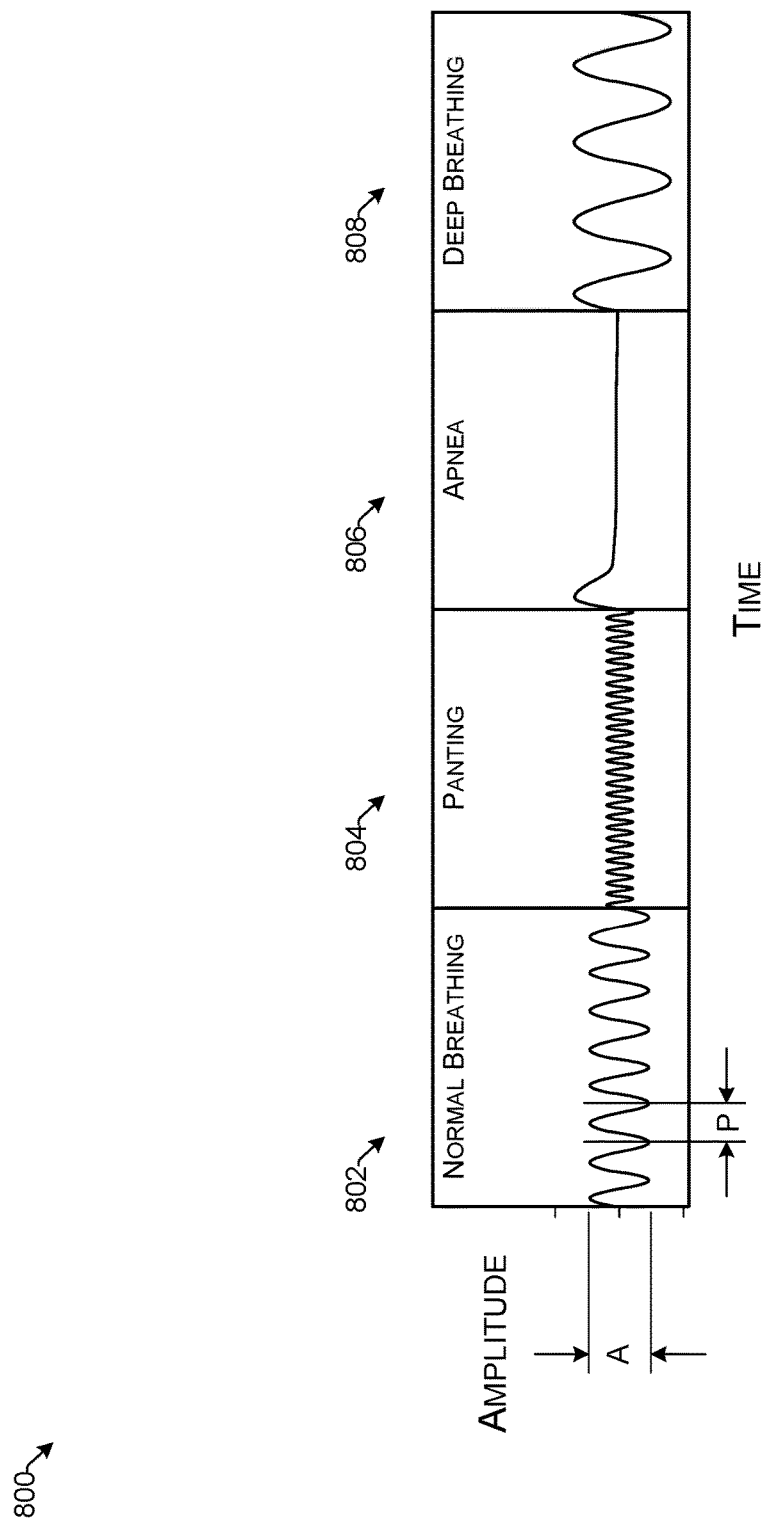
FIG. 8 illustrates examples of different monitored respiration states according to some implementations.

FIG. 8 illustrates examples 800 of different monitored respiration states according to some implementations. The examples 800 are illustrated as wave signals graphed to amplitude versus time in which the amplitude may correspond to a voltage amplitude received from the current amplifier and the peaks and valleys may corresponding to detected inhalation and exhalation, respectively, for a breath. For example, determining each breath may correspond to measuring an amplitude A and a period P of the voltage signal to determine at least partially the respiration rate.

In a first example 802, for normal breathing, the number of breaths over a period of time is determined to be within the normal range for an adult human. In a second example 804, the number of breaths is substantially greater than that for the first example, while the amplitude is substantially smaller, and accordingly the second example is considered to be an abnormal respiration pattern corresponding to panting. In a third example 806, the number of breaths is substantially less than for normal breathing, and thus, the third example 806 is determined to be an abnormal respiration pattern corresponding to apnea. In a fourth example 808, the number of breaths is less over the period of time than the number breaths for normal breathing, and the amplitude of the breaths is substantially larger than that for the first example, which may indicate an abnormal deep breathing pattern. Furthermore, while several example respiration patterns are illustrated in FIG. 8, other possible abnormal breathing patterns will be apparent to those of skill in the art having the benefit of the disclosure herein.

FIG. 9 is a flow diagram illustrating an example process 900 for monitoring respiration according to some implementations. The process 900 may be executed, at least in part, by the respiration monitoring system or other suitable system.

At 902, the system may generate an alternating current signal to one of a first sensor electrode or a second sensor electrode. For example, the first sensor electrode may be associated with a seatbelt and located adjacent to a torso of a vehicle operator of a vehicle. Further, the second sensor electrode may be positioned to be contacted by another body part of the vehicle operator, such as at least one of an arm, hand, leg, or foot, of the vehicle operator.

At 904, the system may receive a capacitance signal from the other one of the first sensor electrode or the second sensor electrode.

At 906, the system may convert the capacitance signal to a voltage signal.

At 908, the system may measure the amplitude and period of the voltage signal to determine at least partially the respiration rate of the vehicle operator.

At 910, the system may determine a respiration pattern based on the respiration rate measured over time.

At 912, based at least partially on determining that the respiration pattern is abnormal, the system may send a control signal to cause the vehicle to at least one of park the vehicle or drive the vehicle autonomously or semi-autonomously. Additionally, or alternatively, the system may send a communication to a remote computing device.

At 914, the system may periodically send respiration data to a remote computing device over a wireless network.

Figure 10:
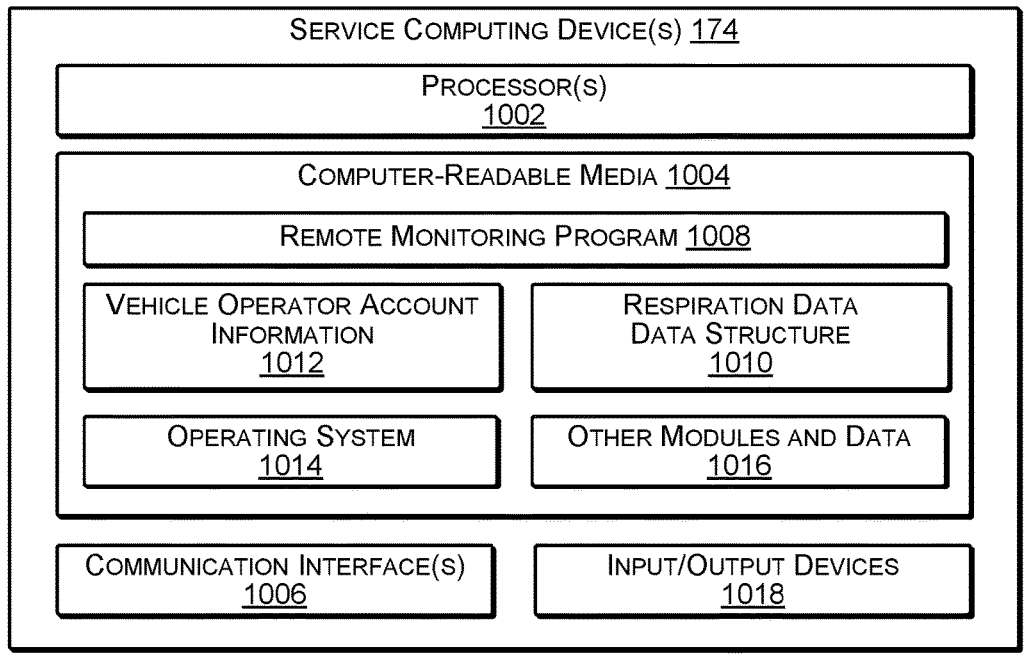
FIG. 10 illustrates select components of an example service computing device according to some implementations.

FIG. 10 illustrates select components of the service computing device(s) 174, which may be used to implement some functionality of the services described herein. As mentioned above, the service computing device(s) 174 may include one or more servers, personal computers, or other types of computing devices that may be embodied in any number of ways. For instance, in the case of a server, the programs, applications, other functional components, and data may be implemented on a single server, a cluster of servers, a server farm, a data center, a cloud-hosted computing service, and so forth, although other computer architectures may additionally or alternatively be used.

Further, while the figures illustrate the components and data of the service computing devices 174 as being present in a single location, these components and data may alternatively be distributed across different computing devices and different locations in any manner. Consequently, the functions may be implemented by one or more service computing devices 174, with the various functionality described above distributed in various ways across the different computing devices. Multiple service computing devices 102 may be located together or separately, and organized, for example, as virtual servers, server banks, and/or server farms. The described functionality may be provided by the servers of a single entity or enterprise, or may be provided by the servers and/or services of multiple different entities or enterprises. Accordingly, implementations herein are not limited to the particular example illustrated.

In the illustrated example, each service computing device 174 includes one or more processors 1002, one or more computer-readable media 1004, and one or more communication interfaces 1006. Each processor 1002 may be a single processing unit or a number of processing units, and may include single or multiple computing units, or multiple processing cores. The processor(s) 1002 may be implemented as one or more microprocessors, microcomputers, microcontrollers, digital signal processors, central processing units, state machines, logic circuitries, and/or any devices that manipulate signals based on operational instructions. For instance, the processor(s) 1002 may be one or more hardware processors and/or logic circuits of any suitable type specifically programmed or otherwise configured to execute the algorithms and processes described herein. The processor(s) 1002 may be configured to fetch and execute computer-readable instructions stored in the computer-readable media 1004, which may program the processor(s) 1002 to perform the functions described herein.

The computer-readable media 1004 may include volatile and nonvolatile memory and/or removable and non-removable media implemented in any type of technology for storage of information, such as computer-readable instructions, data structures, program modules, or other data. Such computer-readable media 1004 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the service computing device 174, the computer-readable media 1004 may be a type of computer-readable storage media and/or may be a tangible non-transitory media to the extent that, when mentioned, non-transitory computer-readable media exclude media such as energy, carrier signals, electromagnetic waves, and signals per se.

The computer-readable media 1004 may be used to store any number of functional components that are executable by the processors 1002. In many implementations, these functional components comprise instructions or programs that are executable by the processors 1002 and that, when executed, specifically configure the one or more processors 1002 to perform the actions attributed above to the service computing device 174. Functional components stored in the computer-readable media 1004 may include a remote monitoring program 1008 that is executed by the processor(s) 1002 to receive communications from a plurality of vehicles. The communications may include respiration data for the vehicle operators. The remote monitoring program 1008 may store the received respiration data in a data structure 1010 in association with a vehicle operator account maintained in vehicle operator account information 1012. In addition, the remote monitoring program 1008 may monitor the received communications for abnormal respiration patterns and/or alerts, and may perform one or more actions based on detecting an abnormal respiration pattern and/or an alert, such as sending a message to an emergency medical vehicle dispatch system, or the like, regarding a location and condition of a vehicle operator having a medical emergency. Additional functional components stored in the computer-readable media 1004 may include an operating system 1014 for controlling and managing various functions of the service computing device(s) 174.

In addition, the computer-readable media 1004 may store data and data structures used for performing the operations described herein. Thus, the computer-readable media 1004 store the respiration data in a data structure 1010 and may store vehicle operator account information 1012, which may be correlated to the respiration data in the data structure 1010. The service computing device(s) 174 may also include or maintain other functional components and data not specifically shown in FIG. 10, such as other modules and data 1016, which may include programs and the data used or generated by the functional components. Further, the service computing devices 174 may include many other logical, programmatic, and physical components, of which those described above are merely examples that are related to the discussion herein.

The communication interface(s) 1006 may include one or more interfaces and hardware components for enabling communication with various other devices, such as over the network(s) 172. For example, communication interface(s) 1006 may enable communication through one or more of the Internet, cable networks, cellular networks, wireless networks (e.g., Wi-Fi) and wired networks (e.g., fiber optic and Ethernet), as well as short-range communications, such as BLUETOOTH®, and the like, as additionally enumerated elsewhere herein.

The service computing device(s) 174 may further be equipped with various input/output (I/O) devices 1012. Such I/O devices 1018 may include a display, various user interface controls (e.g., buttons, keyboard, mouse, touch screen, joystick, etc.), audio speakers, connection ports and so forth.

Various instructions, methods, and techniques described herein may be considered in the general context of computer-executable instructions, such as program modules stored on computer-readable media, and executed by the processor(s) herein. Generally, program modules include routines, programs, objects, components, data structures, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
a first sensor electrode associated with a seatbelt of a vehicle, wherein the first sensor electrode is positioned adjacent to a torso of a vehicle operator;
a second sensor electrode positioned within the vehicle to be proximate to a body part of the vehicle operator during operation of the vehicle;
a capacitance-to-voltage converter that converts a capacitance signal received from one of the first sensor electrode or the second sensor electrode to a voltage signal;
one or more processors; and
one or more non-transitory computer-readable media maintaining executable instructions, which, when executed by the one or more processors, cause the one or more processors to perform operations comprising:
receiving the voltage signal from the capacitance-to-voltage converter; and
determining a respiration rate of the vehicle operator based at least partially on measuring an amplitude and period of the voltage signal.

2. The system as recited in claim 1, wherein the second sensor electrode is located on at least one of:
a steering wheel of the vehicle;
an armrest of the vehicle;
a shift lever of the vehicle;
a foot pedal of the vehicle; or
an upper surface of a bottom seat cushion of the vehicle.

3. The system as recited in claim 1, wherein the second sensor electrode is located on a steering wheel of the vehicle, and further comprises at least one electrode embedded in a portion of a rim of the steering wheel and covered by an insulating material.

4. The system as recited in claim 1, wherein the first sensor electrode is at least one of:
connected to or integral with a lap belt portion of the seatbelt;
connected to or integral with a shoulder belt portion of the seatbelt; or
connected to both the lap belt portion and the shoulder belt portion of the seatbelt, and spanning an area there between.

5. The system as recited in claim 1, further comprising a signal generator for generating an alternating current signal to one of the first sensor electrode or the second sensor electrode.

6. The system as recited in claim 1, the operations further comprising:
determining a respiration pattern based on the respiration rate;
determining that the respiration pattern is abnormal; and
sending at least one of a control signal or a communication based at least partially on determining that the respiration pattern is abnormal.

7. A method comprising:
generating an alternating current signal to one of a first sensor electrode or a second sensor electrode, wherein the first sensor electrode is associated with a seatbelt and located adjacent to a torso of a vehicle operator of a vehicle, and the second sensor electrode is positioned to be proximate to at least one of an arm, hand, leg, or foot, of the vehicle operator;
receiving from the other one of the first sensor electrode or the second sensor electrode, a signal indicative of a capacitance; and
determining, by a processor, a respiration rate based at least partially on the signal indicative of the capacitance,
wherein there are multiple second sensor electrodes, the method further comprising:
determining that the vehicle operator is contacting a certain one of the second sensor electrodes;
determining that the vehicle operator has contacted the certain second sensor electrode for a threshold time; and
receiving the signal indicative of the capacitance from the certain second sensor electrode.

8. The method as recited in claim 7, further comprising:
determining a respiration pattern based on the respiration rate;
determining that the respiration pattern is abnormal; and
performing at least one action based at least partially on determining that the respiration pattern is abnormal.

9. The method as recited in claim 8, wherein performing at least one action based at least partially on determining that the respiration pattern is abnormal comprises sending a control signal to cause the vehicle to at least one of park the vehicle, or drive the vehicle autonomously or semi-autonomously.

10. The method as recited in claim 7, wherein performing at least one action based at least partially on determining that the respiration pattern is abnormal comprises sending a communication to a service computing device over a network.

11. The method as recited in claim 7, further comprising:
converting the signal indicative of the capacitance into a voltage signal; and
measuring an amplitude and period of the voltage signal to determine at least partially the respiration rate.

12. The method as recited in claim 7, further comprising:
storing the respiration rate as respiration data; and
sending the respiration data over a network to a computing device.

13. An apparatus comprising:
a first sensor electrode associated with a seatbelt for restraining a vehicle operator of a vehicle;
a second sensor electrode positioned within the vehicle to be proximate to a body part of the vehicle operator;
a signal generator that generates a signal to one of the first sensor electrode or the second sensor electrode;
a capacitance-to-voltage converter that converts a capacitance signal received from the other one of the first sensor electrode or the second sensor electrode to a voltage signal; and
a voltage measurement circuit that determines, at least in part, a respiration rate based on an amplitude and period of the voltage signal received from the capacitance-to-voltage converter.

14. The apparatus as recited in claim 13, further comprising a processor, wherein the voltage measurement circuit is included in or is associated with the processor, the processor configured by executable instructions to determine, at least in part, the respiration rate, and to further determine, at least in part, a respiration pattern based on the respiration rate.

15. The apparatus as recited in claim 13, further comprising a memory and a transceiver, wherein the respiration rate is stored in the memory and sent by the transceiver over a wireless network to a computing device.

16. The apparatus as recited in claim 13, wherein the first sensor electrode is at least one of:
connected to or integral with a lap belt portion of the seatbelt;

connected to or integral with a shoulder belt portion of the seatbelt; or connected to both the lap belt portion and the shoulder belt portion of the seatbelt, and spanning an area there between.

17. The apparatus as recited in claim 13, wherein the second sensor electrode is located on at least one of:
a steering wheel of the vehicle;
an armrest of the vehicle;
a shift lever of the vehicle;
a foot pedal of the vehicle; or
an upper surface of a bottom seat cushion of the vehicle.

18. The apparatus as recited in claim 13, wherein the second sensor electrode is located on a steering wheel of the vehicle, and further comprises at least one electrode embedded in a portion of a rim of the steering wheel and covered by an insulating material.

\* \* \* \* \*